US005629464A

United States Patent [19]
Bach et al.

[11] Patent Number: 5,629,464
[45] Date of Patent: May 13, 1997

[54] METHOD FOR FORMING UNSATURATED ORGANICS FROM ORGANIC-CONTAINING FEED BY EMPLOYING A BRONSTED ACID

[75] Inventors: Robert D. Bach, Gross Pointe, Mich.; Christopher J. Nagel, Wayland, Mass.

[73] Assignee: Molten Metal Technology, Inc., Waltham, Mass.

[21] Appl. No.: 172,582

[22] Filed: Dec. 23, 1993

[51] Int. Cl.$^6$ .................................................. C07C 4/02
[52] U.S. Cl. .................... 585/634; 585/652; 585/653; 585/608; 208/405
[58] Field of Search .................... 208/400, 401, 208/402, 403, 404, 406, 405; 585/241, 512, 540, 613, 634, 643, 650, 652, 608; 588/201

[56] References Cited

U.S. PATENT DOCUMENTS

| | | | |
|---|---|---|---|
| 2,858,255 | 10/1958 | Segui et al. | 202/219 |
| 3,974,206 | 8/1976 | Tortsumi | 585/241 X |
| 3,996,022 | 12/1976 | Larsen | 44/1 D |
| 4,012,457 | 3/1977 | Bredeson et al. | 260/683 |
| 4,552,667 | 11/1985 | Schultz | 210/757 |
| 4,574,038 | 3/1986 | Wan | 204/162 |
| 4,574,714 | 3/1986 | Bach et al. | 110/346 |
| 4,666,696 | 5/1987 | Shultz | 423/659 |
| 4,769,507 | 9/1988 | Murib et al. | 585/500 |
| 5,177,304 | 1/1993 | Nagel | 588/201 |
| 5,191,154 | 3/1993 | Nagel | 588/201 |

FOREIGN PATENT DOCUMENTS

| | | |
|---|---|---|
| 0067491A2 | 12/1982 | European Pat. Off. . |
| 44-11648 | 5/1969 | Japan . |
| 936899 | 9/1963 | United Kingdom . |
| 1350612 | 4/1974 | United Kingdom . |
| 399526 | 9/1993 | United Kingdom . |

OTHER PUBLICATIONS

Haggin, J., "Growth and Dissociation of Metal-Carbon Nanocrystals Probed," *Chem. & Eng. News*, pp. 29–32, Oct. 25, 1993.

Haggin, J., "European Conference Draws Attention to Fundamental Role of Catalysis," *Chem. & Eng. News*, pp. 26–30, Oct. 18, 1993.

Layman, P.L., "Advances in Feedstock Recycling Offer Help with Plastic Waste," *Chem. & Eng. News*, pp. 11–14, Oct. 4, 1993.

Satterfield, C.N., "Acid and Zeolite Catalysts," In Gail F. Nalven (Ed.), *Heterogeneous Catalysis in Industrial Practice*, 2nd Ed., (NY: McGraw–Hill), pp. 209–266, pp. 339–417, (1991).

Jebens, A.M., "CEH Marketing Research Report, Ethylene," *Chemical Economics Handbook–SRI International*, (Report Olefins 432.0000 A) Sep., 1992.

Adams et al., "Dehydrogenation and Coupling Reactions in the Presence of Iodine and Molten Salt Hydrogen Iodide Acceptors," *Journal of Organic Chemistry*, 42(1):1–6 (1977).

Saito et al., "Dehydrogenation of Some Alcohols by the Molten Metal Catalysts," *Bulletin of the Japan Petroleum Institute*, 42 (2):169–173 (1972).

Kashiwadate, et al., "The Dehydrogenation of Butyl Alcohols by the Molten-metal Catalysts," *Bulletin of the Chemical Society of Japan*, 44(11):3004–3009 (1971).

(List continued on next page.)

*Primary Examiner*—Helane Myers
*Assistant Examiner*—Bekir L. Yildirim
*Attorney, Agent, or Firm*—Hamilton, Brook, Smith & Reynolds, P.C.

[57] ABSTRACT

The invention relates to a method for producing an unsaturated organic compound from an organic-containing feed. The method includes providing a reactor containing a liquid bath which includes a Bronsted acid that can protonate an organic component of the organic-containing feed. The feed is directed into the liquid bath at a rate which causes the Bronsted acid to protonate the organic component. Conditions are established and maintained in the reactor which cause the protonated organic component to fragment and form a carbenium ion and an unsaturated organic compound, whereby the unsaturated organic compound is discharged from the liquid bath.

24 Claims, 1 Drawing Sheet

OTHER PUBLICATIONS

Benesi et al., "Surface Acidity of Solid Catalysts," *Advances in Catalysis*, 27:97–182 (1978).

Jerry March, "Advanced Organic Chemistry", 1977, McGraw–Hill, pp. 151–160.

Forni, Lucio, "Comparison of the Methods for the Determination of Surface Acidity of Solid Catalysts," *Catalysis Reviews*, 8(1):65–115 (1973).

Goldstein, Marvin S., "Measurement of Acidity of Surfaces," Academic Press, pp. 361–401 (1968).

Hashimoto et al., "Measurement of Bronsted Acid and Lewis Acid Strength Distributions of Solid Acid Catalysts Using Chemisorption Isotherms of Hammett Indicators," *Ind. Eng. Chem. Res.*, 27(10):1792–1797 (1988).

Jacobs, Peter A., "The Measurement of Surface Acidity," Dekker, pp. 367–405 (1984).

Tanabe et al., "Design of Sulfur–Promoted Solid Superacid Catalyst," *Successful Design of Catalysts*, pp. 99–110 (1988).

Unger et al., "Examination and Standardisation of Amine Titration in Surface Acidity Measurements of Silicas, Aluminas and Synthetic Zeolites," *J. Chem. Tech. Biotechnol.*, 31:435–469 (1981).

March, Jerry, "Aromatic Eletrophilic Substitution," In *Advanced Organic Chemistry: Reactions, Mechanisms, and Structure*, Chapter Eleven (McGraw–Hill), pp. 376–441 (1977).

March, Jerry, "Eliminations," In *Advanced Organic Chemistry: Reactions, Mechanisms, and Structure*, Chapter Seventeen (McGraw–Hill), pp. 727–780 (1977).

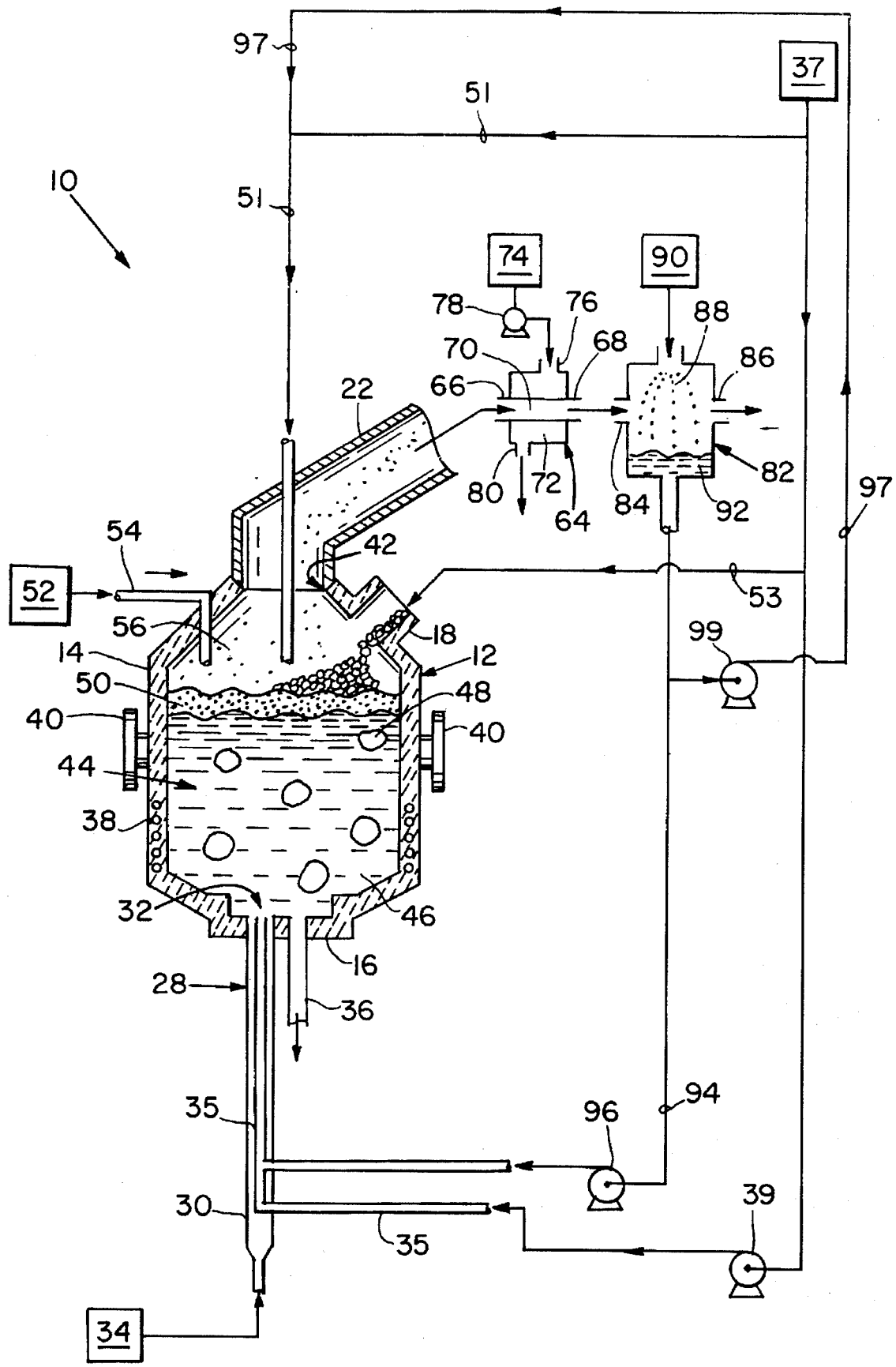

METHOD FOR FORMING UNSATURATED ORGANICS FROM ORGANIC-CONTAINING FEED BY EMPLOYING A BRONSTED ACID

BACKGROUND OF THE INVENTION

Considerable research has been conducted recently in the area of producing alkenes for use as industrial raw materials. Among the many uses of such commodity chemicals include plastic and fibers for consumption in packaging, transportation and construction industries. Of particular interest are areas of research focusing on production of alkenes, such as ethylene, which is consumed principally in the manufacture of polyethylene, and substituted alkenes, such as ethylene dichloride and vinyl chloride. Ethylene is also employed in the production of ethylene oxide, ethyl benzene, ethylene dichloride, ethylene-propylene elastomers and vinyl acetate.

The primary sources of alkenes, such as ethylene, include: steam cracking of organics, such as gas oils; off-gas from fluid catalytic cracking (FCC) in oil refineries, catalytic dehydration of alcohols; and recovery from coal-derived synthesis gas. However, the worldwide demand for alkenes is extraordinary: the short fall in worldwide supply of ethylene alone was estimated in 1991 to be about 2.3 million tons, as determined by the Chemical Economics Handbook, SRI International (1992). Further, known methods for producing alkenes have significant drawbacks. For example, organic steam cracking, which accounts for about 100% of ethylene production in the United States, is a mature technology which is highly sensitive to process variables, such as cracking severity, residence time and organic partial pressure, as well as plant economics and price fluctuation. Other methods, such as alkene cracking over a solid support, can cause "coking up," which requires frequent burnout of the solid support to continue processing. In addition, such processes are facing increasing environmental regulatory pressure to control systematic problems, such as leaks and failure from related equipment and safety concerns associated with alkene cracking.

Other listed production methods have even greater limitations. The availability of FCC off-gas, for example, generally prohibits its use as an economically viable feed stock. Catalytic dehydration of alcohols is effectively limited to certain countries that have large amounts of readily available fermentation raw material. Also, known methods for production of alkenes from other sources, such as coal and coal-derived naphtha and methanol are, at best, only marginally commercially viable.

Therefore, a need exists for an improved method of producing alkenes which significantly reduces or eliminates the above-mentioned problems.

SUMMARY OF THE INVENTION

The invention relates to a method for producing an unsaturated organic compound from an organic-containing feed.

The method includes providing a reactor containing a liquid bath which includes a Bronsted acid that can protonate an organic component of the organic-containing feed. The feed is directed into the liquid bath at a rate which causes the Bronsted acid to protonate said organic component. Conditions are established and maintained in the reactor which cause the protonated organic component to fragment and form a carbenium ion and an unsaturated organic compound, whereby the unsaturated organic compound is discharged from the liquid bath.

The present invention has many advantages. For example, the molten bath can operate as a uniform energy source for the reaction, thereby providing good control over reaction conditions during production of components, including unsaturated alkenes, such as ethylene. Also, high yields of ethylene are obtained by the present invention. The present method is a heterogeneous catalytic recycling process, employing solution equilibria to synthesize commercial products from a wide variety of organic feeds, including most hazardous industrial wastes. The present invention also has the ability to sustain high product quality with varying feed heterogeneity, including chemical or physical complexity. Also, the method has the capability to maintain a desirable processing environment with little or no requirement for feed characterization or pretreatment. Further, the present invention has the ability to recover and recycle volatile and nonvolatile metals.

BRIEF DESCRIPTION OF THE DRAWINGS

The FIGURE is a schematic representation of one embodiment of apparatus suitable for conducting the method of the invention.

DETAILED DESCRIPTION OF THE INVENTION

The features and other details of the method of the invention will now be more particularly described with reference to the accompanying figures and pointed out in the claims. It will be understood that particular embodiments of the invention are shown by way of illustration and not as limitations of the invention. The principal functions of this invention can be employed in various embodiments without departing from the scope of the invention.

The present invention generally relates to a method for forming unsaturated organics from an organic-containing feed by employing a Bronsted acid. The feed can be an organic waste stream and the Bronsted acid can be a component of a molten bath. Processes for decomposing waste in molten baths are disclosed in U.S. Pat. Nos. 4,574,714, 5,177,304, and 4,602,574 which are incorporated herein by reference.

In one embodiment of the invention, illustrated in the FIGURE, system 10 includes reactor 12. Examples of suitable vessels include those described in U.S. Ser. No. 08/041,490 and U.S. Ser. No. 08/041,405, the teachings of which are incorporated by reference, and reactors which are described in U.S. Pat. No. 4,574,714, U.S. Pat. No. 5,177,304, and U.S. Pat. No. 4,602,574. Reactor 12 has an upper portion 14 and a lower portion 16. Feed inlet 18 at upper portion 14 of reactor 12 is suitable for directing feed into reactor 12. Off-gas outlet 22 extends from upper portion 14 and is suitable for conducting an off-gas out of reactor 12.

It is to be understood that the feed stream is generally introduced to bath 44 without injection of a coolant if reaction of the feed is endothermic. However, tuyere 28 is dimensioned and configured for conjointly and continuously introducing a suitable feed stream and coolant into reactor 12. Tuyere 28 includes coolant tube 30 and feed inlet tube 35. Coolant tube 30 extends from coolant source 34 to reactor 12. Feed inlet tube 35 extends from feed source 37 to tuyere 28. Feed inlet tube 35 is disposed at tuyere opening 32. Pump 39 is disposed at tuyere 28 to direct a suitable feed stream from feed source 37 and through tuyere opening 32 into reactor 12. It is to be understood that an oxidant can also be fed to reactor 12 through tuyere 28 and/or at other locations within reactor 12, as are taught in U.S. Pat. No. 5,191,154, the teachings of which are incorporated by reference.

It is also to be understood that more than one tuyere 28 can be disposed in reactor 12 and that concentric, or multiple concentric tuyeres, can be employed for separate introduction of the feed stream into reactor 12. Further, it is to be understood that feed can be introduced into reactor 12 by other suitable methods, such as by employing a lance, etc.

Bottom-tapping spout 36 extends from lower portion 16 and is suitable for removal of at least a portion of a molten bath from reactor 12. Additional drains can be provided as a means of continuously or intermittently removing distinct molten phases. Material can also be removed by other methods, such as are known in the art. For example, material can be removed from reactor 12 by rotating vessel 12 and employing a launder, not shown, extending from feed inlet 18. Alternatively, the launder can extend into reactor 12 through a tap hole, also not shown.

Induction coil 38 is disposed at lower portion 16 for heating reactor 12 or for initiating generation of heat within reactor 12. Trunions 40 are disposed at reactor 12 for manipulation of reactor 12. Seal 42 is disposed between reactor 12 and off-gas outlet 22 and is suitable for allowing partial rotation of reactor 12 about trunions 40 without breaking seal 42. Alternatively, reactor 12 does not include trunions 40 or seal 42 and does not rotate.

Bath 44 is disposed within reactor 12. In one embodiment, bath 44 includes a Bronsted acid which causes at least a portion of a organic in the injected feed to be reformed to at least one unsaturated alkene of lower molecular weight, such as ethylene, under the operating conditions of system 10. In one embodiment, the components of bath 44 generally have a temperature in the range of between about 1,000° and 2,000° C. The temperature of bath 44 is sufficient to cause organic components of the injected feed to be reformed and subsequently discharged from bath 44 as at least one unsaturated organic of lower molecular weight.

In a particularly preferred embodiment, the operating conditions of the bath which cause the reformation include, for example, temperatures which prevent substantial degradation of organic compounds. Also, the required residence times of the feed in the bath of molten metal are substantially shorter than are those typically employed to thermally decompose organic-containing feeds.

Further, the amount of carbon in bath 44 can be controlled, for example: by the rate of introduction of the feed stream, to bath 44; by controlling the rate of removal of off-gas from bath 44; by controlling system conditions, e.g., temperature, of system 10; by controlling the relative amounts of other components in bath 44; etc.

Examples of suitable compositions in bath 44 include silicon and aluminum-containing compositions wherein the ratio of aluminum to silicon is less than about one. Also, it is to be understood that bath 44 can include oxides of the molten metals. As disclosed in U.S. Pat. No. 5,177,304, the teachings of which are incorporated herein, bath 44 can include more than one phase of molten metal. In one embodiment, bath 44 is formed of a vitreous phase which includes at least one metal oxide. In another embodiment, the vitreous phase can include at least one salt. Alternatively, a substantial portion of bath 44 can be of elemental metal.

Bath 44 can be formed by at least partially filling reactor 12 with a suitable mixture of silicon dioxide and at least one oxide selected from the group consisting of aluminum, boron, calcium, zirconium, titanium, chromium, sulfur and zinc. Alternatively bath 44 can be formed by at least partially filling reactor 12 with aluminum oxide and at least one oxide selected from the group consisting of silicon, boron, calcium, magnesium, zirconium, titanium, chromium, sulfur and zinc.

In one specific embodiment, bath 44 is formed by combining calcium oxide and aluminum oxide ($Al_2O_3$) in a stoichiometric ratio of between about 0.25 and one. The components are then heated to a suitable temperature by activating induction coil 38 or by some other suitable means, not shown. Examples of suitable means include plasma torch, electric arc, etc.

Upon heating the contents of reactor 12 they combine to form a Lewis acid. An example of such a Lewis acid is an aluminum (III) silyltrioxide species containing an empty orbital on the aluminum metal center, and has the following structural formula:

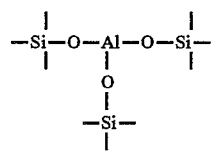

In an alternative embodiment, the Lewis acid of bath 44 is a halide of antimony or arsenic.

The Lewis acid of bath 44 is then reacted with a relatively weak Bronsted acid, such as water, to form a more reactive Bronsted acid. For example, the Bronsted acid can be formed by directing water into bath 44 from source 52 through line 54 to react with the Lewis acid, or by maintaining a sufficient water partial pressure above bath 44. Alternatively, water can be directed into bath 44 by submerged injection means, not shown.

In this embodiment, the reaction of an aluminum and silicon-containing Lewis acid with water can be represented by the following equation:

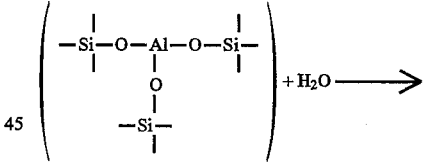

Because of an increased stability of the resulting aluminate anion relative to a hydroxide ion, the newly-formed Bronsted acid is much more acidic than water.

Alternatively, bath 44 is a liquid. For example, the Lewis acid can react with halide anion-containing Lewis base, i.e., a relatively weak Lewis base, such as ammonium fluoride or ammonium chloride, which can be directed into reactor 12 by a suitable means. In one embodiment, formation of the strong Bronsted acid by a Lewis acid/Lewis base reaction can be represented as follows:

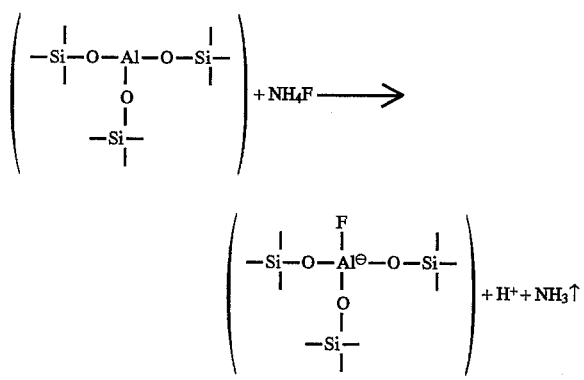

In one embodiment, the viscosity of at least one phase of bath 44 is less than about ten centipoise at the operating conditions of system 10. In another embodiment, the viscosity of at least one phase of bath 44 is less than about one hundred poise at the operating conditions of system 10.

Vitreous layer 50 is disposed on bath 44. Vitreous layer 50 is substantially immiscible with bath 44. Alternatively, system 10 does not include vitreous layer 50. In another embodiment, vitreous layer 50 has a lower thermal conductivity than that of bath 44. Radiant loss of heat from bath 44 can thereby be reduced to significantly below the radiant heat loss from bath 44 when no vitreous layer 50 is present.

Examples of suitable metal oxides of vitreous layer 50 include titanium oxide ($TiO_2$), zirconium oxide ($ZrO_2$), aluminum oxide ($Al_2O_3$), magnesium oxide (MgO), calcium oxide (CaO), silica ($SiO_2$), etc. Other examples of suitable components of vitreous layer 50 include halogens, sulfur, phosphorus, heavy metals, etc. It is to be understood that vitreous layer 50 can include more than one metal oxide. Vitreous layer 50 can contain more than one phase. Typically, vitreous layer 50 is substantially fluid and other gases can press across vitreous layer 50 from bath 44.

Feed, such as a waste in solid, liquid, or gaseous form, is directed from feed source 37 into a reaction zone with reactor 12. The reaction zone is defined to be the region in which the production formation reaction(s) occur. It can include the volume within reactor and subsequent off-gas handling equipment. The environment supporting reaction includes the Bronsted Acid system, the gas liquid interface, and the gas space above the Bronsted Acid system which contains acid vapor and reactive acid particles and droplets (caused by entrainment).

The feed can be introduced to reactor 12 through line 35, line 51 and/or line 53. The feed includes an organic component. Examples of suitable organics include those containing both alkyl and aryl substituents. Specific examples of suitable organic components also include alkenes and polyenes. Examples of suitable feeds include "dirty" crude oil, bottoms from oil refineries, oil shales, hazardous wastes, waste plastics, tires, etc.

In one embodiment, the feed is injected into bath 44 as a component of a feed stream that also includes an inert gas component, such as argon. In one example, the feed stream can be formed by vaporizing liquid organic feed in the presence of an inert gas. The amount of volatilized feed component in the feed stream can be, for example, in the range of between about five and forty percent, by volume.

It is to be understood that inorganic components can also be included in the feed stream for introduction and chemical reaction in system 10. Suitable examples of inorganic feed components include, but are not limited to, metals and their oxides, sulfides and halides. In addition to organics, the organic components of the feed stream can also include atomic constituents, such as halides, metals, etc.

The feed stream directed into reactor 12 combines with bath 44 and can also combine with vitreous layer 50. The feed stream and coolant are directed into bath 44 through tuyere 28. The feed stream can also be directed into reactor 16 from feed source 37 through conduit 51. Conduit 51 discharges the feed beneath the surface of bath 44. Contact of the feed with bath 44 or vitreous layer 50 exposes the feed to conditions sufficient to form at least one unsaturated organic of reduced molecular weight. Optionally, reformation of the organic component of the feed can occur above bath 44, such as by contact of components of bath 44 that are entrained in gas flow through or above bath 44. In one embodiment, for example, substituted splashing of bath 44 is caused in reactor 12 by rapid injection of feed or other materials through tuyeres into bath 44. This splashing effect can cause significantly increased surface contact between gases in reactor 12 and bath 44, thereby significantly increasing the rate of reformation of organic feed components to unsaturated organic compounds.

It is believed that the Bronsted acid of bath 44 reacts with an organic, such as an alkane, to form a hypervalent carbonium ion, as shown below:

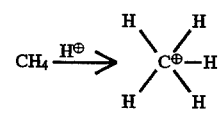

Alternatively, the Bronsted acid can react with an alkene to form a trivalent carbenium ion, as shown below:

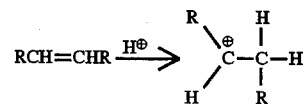

where "R" is an alkyl group. The carbonium ions and the carbenium ions can undergo subsequent rearrangements or sigma bond cleavage to produce lower molecular weight fragments, by the following mechanisms:

carbonium:

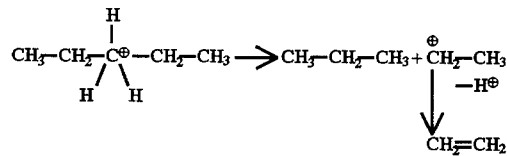

carbenium:

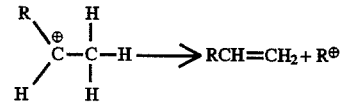

The lower-molecular weight fragments include unsaturated organics that are discharged from bath 44.

If necessary, a coolant can be employed to cool tuyere 28. Examples of suitable coolants include steam, methane ($CH_4$), hydrogen gas ($H_2$), natural gas, etc.

Gaseous layer 56 is formed over vitreous layer 50. In one embodiment, gaseous layer 56 extends from upper portion 14 of reactor 12 through off-gas outlet 22 to scrubber 82. A reaction zone within system 10 includes bath 44, vitreous layer 50 and gaseous layer 56. Reactants can be introduced anywhere within the reaction zone. Gaseous layer 56 includes off-gas formed in bath 44 and in vitreous layer 50. The off-gas can also include at least on intermediate component which has been entrained or which has been volatilized before reformation to a shorter-chain unsaturated organic is complete.

Off-gas formed in reactor 12 is conducted from the reaction zone through off-gas outlet 22 to heat exchanger 64. Heat exchanger 64 can be any suitable heat exchanger for cooling off-gas discharged from reactor 12. Examples of suitable heat exchangers include water-cooled hoods, shell-and-tube heat exchangers, fluid beds, etc. Examples of off-gas components include unreacted or fragmented portions of the organic feed components.

The off-gas is conducted into heat exchanger 64 through heat exchanger off-gas inlet 66 and then through heat-exchanger off-gas outlet 68. Optionally, the off-gas is cooled in heat exchanger 64 by conducting the off-gas through and off-gas side 70 of heat exchanger 64 and by directing a suitable cooling medium through a medium-side 72 of heat exchanger 64. Examples of suitable cooling mediums include, for example, water, ethylene glycol, ethyl benzene, alcohols, etc. The cooling medium is directed from cooling medium source 74 through cooling medium inlet 76 of heat exchanger 64 by a suitable means, such as by use of pump 78 disposed between cooling medium source 74 and heat exchanger 64. The cooling medium is directed through the medium side 72 of heat exchanger 64, thereby cooling the off-gas, and then directed out of heat exchanger 64 through cooling medium outlet 80.

The off-gas is directed out of heat exchanger off-gas outlet 68 to a suitable separating means for exposing the off-gas to conditions sufficient to remove at least a portion of an intermediate component from the off-gas. In one illustration, the separating means is scrubber 82. The off-gas is directed through scrubber off-gas inlet 84 and then through scrubber 82 to scrubber off-gas outlet 86.

Scrubber fluid 88 is directed from scrubber fluid source 90 to scrubber 82 by a suitable means, such as by gravity or by a pump, not shown. Scrubber fluid 88 is introduced to scrubber 82 at a temperature suitable for removing at least a portion of a component from the off-gas.

It is to be understood that additional separating means can be employed to separate components from off-gas discharged from reactor 16. For example, a suitable cyclone separator, not shown, and a suitable spray drier, also not shown, can be disposed between heat exchanger 64 and scrubber 82.

Liquid composition 92 is formed by scrubbing of the off-gas with scrubber fluid 88. Liquid composition 92 is directed from scrubber 82 to reactor 12. In one embodiment, liquid composition 92 is pumped through piping 94 by pump 96 to the feed inlet tube 35. Examples of suitable pumps include a centrifugal pump, a positive displacement pump, etc. Liquid composition 92 is thereby combined with the feed for introduction into bath 44 through tuyere 28. In another embodiment, liquid composition 92 is directed through piping 97 by pump 99 to conduit 51. Liquid composition 92 is thereby combined with the feed stream for introduction into reactor 12 and onto bath 44.

At least a portion of the off-gas components are thereby returned in liquid composition 92 from the off-gas to bath 44. A substantial portion of the discharged feed components are then chemically reformed to unsaturated organics, such as ethylene. Chemical reaction of the feed components in system 10 is thereby controlled.

EQUIVALENTS

Those skilled in the art will recognize, or be able to ascertain using no more than routine experimentation, many equivalents of the invention described specifically herein. Such equivalents are intended to be encompassed in the scope of the following claims.

We claim:

1. A method for producing an unsaturated organic compound from an alkane component of an organic-containing feed, comprising the steps of:
   a) providing a reactor containing a bath, said bath comprising a Bronsted acid which can protonate an alkane component of the organic-containing feed;
   b) directing the feed into contact with the bath at a rate which causes the Bronsted acid to protonate said alkane component; and
   c) establishing and maintaining conditions in the reactor which cause the protonated alkane component to fragment and form a carbenium ion and an unsaturated organic component.

2. A method of claim 1 wherein the bath is formed by a method, comprising the steps of:
   a) forming an inorganic phase in the reactor, said inorganic phase comprising a Lewis acid; and
   b) directing a reagent into contact with the Lewis acid, said reagent reacting with the Lewis acid to form said Bronsted acid.

3. A method of claim 2 wherein said reagent is a second, relatively weak Lewis base.

4. A method of claim 3 wherein the relatively weak Lewis base is a halide anion containing compound.

5. A method of claim 4 wherein the halogen-compound is an ammonium halide.

6. A method of claim 5 wherein the ammonium halide is ammonium fluoride.

7. A method of claim 5 wherein the ammonium halide is ammonium chloride.

8. A method of claim 2 wherein the inorganic phase is formed by directing silicon dioxide into the reactor.

9. A method of claim 8 further comprising the step of directing into the reactor at least one oxide selected from the group consisting of Al, B, Ca, Mg, Zr, Ti, Cr, S and Zn.

10. A method of claim 2 wherein the inorganic phase is formed by directing aluminum oxide into the reactor.

11. A method of claim 10 further comprising the step of directing into the reactor at least one oxide selected from the group consisting of Si, B, Ca, Mg, Zr, Ti, Cr, S, and Zn.

12. A method of claim 2 wherein the inorganic phase is formed by directing silicon dioxide and aluminum oxide into the reactor.

13. A method of claim 12 wherein the stoichiometric ratio of aluminum to silicon in the reactor is less than about one.

14. A method of claim 2 wherein the inorganic phase is formed by directing calcium oxide and aluminum oxide into the reactor.

15. A method of claim 14 wherein the stoichiometric ratio of calcium to aluminum is in the range of between about 0.25 and one.

16. A method of claim 2 wherein the inorganic phase comprises antimony.

17. A method of claim 2 wherein the inorganic phase comprises arsenic.

18. A method of claim 17 wherein the bath further comprises a molten metal phase.

19. A method of claim 18 wherein the alkane component of the feed further comprises an aryl substituent.

20. A method for producing an unsaturated organic compound from an alkane component of an organic-containing feed, comprising the steps of:

a) providing a reactor containing a bath, said bath comprising a ceramic phase and a molten metal phase, the ceramic phase comprising a Bronsted acid which can protonate an alkane component of the organic-containing feed;

b) directing the feed into contact with the bath at a rate which causes the Bronsted acid to protonate said alkane component; and c) establishing and maintaining conditions in the reactor which cause the protonated alkane component to fragment and form a carbenium ion and an unsaturated organic compound.

21. A method of claim 20 wherein said reagent is a second, relatively weak Bronsted acid.

22. A method of claim 21 wherein the reagent which reacts with the Lewis acid to form a Bronsted acid is water.

23. A method of claim 22 wherein the Bronsted acid is formed by directing water into the reactor above the bath in an amount sufficient to react with said Lewis acid and thereby form said Bronsted acid.

24. A method of claim 20 wherein the ceramic phase is a liquid.

* * * * *